(12) United States Patent
Tanner et al.

(10) Patent No.: US 9,192,552 B2
(45) Date of Patent: Nov. 24, 2015

(54) PERSONAL CARE COMPOSITIONS WITH IMPROVED SOLUBILITY OF A SOLID UV ACTIVE

(75) Inventors: Paul Robert Tanner, Lebanon, OH (US); Rebecca Ann Finley, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 416 days.

(21) Appl. No.: 13/177,862

(22) Filed: Jul. 7, 2011

(65) Prior Publication Data
US 2013/0011346 A1 Jan. 10, 2013

(51) Int. Cl.
*A61K 8/00* (2006.01)
*A61K 8/35* (2006.01)
*A61K 8/44* (2006.01)
*A61K 8/49* (2006.01)
*A61Q 17/04* (2006.01)
*A61K 8/40* (2006.01)

(52) U.S. Cl.
CPC ... *A61K 8/35* (2013.01); *A61K 8/40* (2013.01); *A61K 8/445* (2013.01); *A61K 8/4966* (2013.01); *A61K 8/4973* (2013.01); *A61Q 17/04* (2013.01); *A61K 2800/49* (2013.01)

(58) Field of Classification Search
CPC . A61K 8/4973; A61K 2800/49; A61K 31/12; A61K 31/352; A61K 8/35; A61K 8/40; A61K 8/44; A61K 8/445; A61K 8/4966; A61K 8/63; A61K 8/678; A61Q 17/04; A61Q 19/00
See application file for complete search history.

(56) References Cited

U.S. PATENT DOCUMENTS

| | | |
|---|---|---|
| 3,755,560 A | 8/1973 | Dickert |
| 4,421,769 A | 12/1983 | Dixon |
| 5,413,781 A | 5/1995 | Giwa-Agbomeirele |
| 5,686,082 A | 11/1997 | N'Guyen |
| 5,725,845 A | 3/1998 | Krog |
| 5,993,789 A | 11/1999 | Bonda |
| 6,113,931 A | 9/2000 | Bonda |
| 6,126,925 A | 10/2000 | Bonda |
| 6,284,916 B1 | 9/2001 | Bonda |
| 6,872,401 B2 | 3/2005 | Seyler |
| 7,357,919 B2 | 4/2008 | Candau |
| 2003/0108492 A1 | 6/2003 | Chaudhuri |
| 2003/0157035 A1 | 8/2003 | Chaudhuri |
| 2004/0057912 A1 | 3/2004 | Bonda |
| 2004/0057914 A1 | 3/2004 | Bonda |
| 2004/0057916 A1 | 3/2004 | Bonda |
| 2004/0062726 A1 | 4/2004 | Bonda |
| 2004/0175347 A1 | 9/2004 | Bissett |
| 2005/0220727 A1 | 10/2005 | Lupia |
| 2006/0263309 A1 | 11/2006 | Bissett |
| 2006/0275237 A1 | 12/2006 | Bissett |
| 2007/0020220 A1 | 1/2007 | Osborne |
| 2007/0185038 A1 | 8/2007 | Bissett |
| 2008/0019930 A1 | 1/2008 | Candau |
| 2008/0145324 A1 | 6/2008 | Richard |
| 2010/0112100 A1 | 5/2010 | Willemin |
| 2011/0117036 A1* | 5/2011 | Chaudhuri ............ 424/60 |
| 2013/0011347 A1 | 1/2013 | Tanner |

FOREIGN PATENT DOCUMENTS

| | | |
|---|---|---|
| DE | 19651055 | 6/1998 |
| DE | 19723732 | 5/2011 |
| WO | 2004/024798 | 3/2004 |
| WO | WO2006/103338 | 10/2006 |
| WO | WO2009/129627 | 10/2009 |
| WO | WO2013/017260 | 2/2013 |

OTHER PUBLICATIONS

U.S. Appl. No. 13/177,880, filed Jul. 7, 2011, Paul Robert Tanner, et al.
Synovea DOI: "A Cost-Effective Solution in Improving Skin Hydration, Barrier Homeostasis & Epidermal Architecture"; www.sytheonltd.com, retrieval date Sep. 30, 2011; 1 page.
All Office Actions and Responses beginning Sep. 18, 2012 for U.S. Appl. No. 13/177,880, filed Jul. 7, 2011.
"Orange Blossom & Hazelnut Moisturizing Body Lotion" www.mitel.com; May 2011.
International Preliminary Report on Patentability; PCT/US2012/045646; International Filing Date Jul. 6, 2012; 12 pages.

* cited by examiner

*Primary Examiner* — Lezah Roberts
*Assistant Examiner* — Nannette Holloman
(74) *Attorney, Agent, or Firm* — Carl J. Roof; John G. Powell; Eric T. Addington

(57) ABSTRACT

A personal care composition may have an isosorbide diester having the formula:

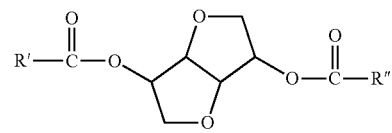

wherein R' and R" are independently selected from a straight or branched $C_{1-30}$ chain, which may be saturated or unsaturated. The composition may further comprise a solid UV active soluble in the isosorbide diester and a dermatologically acceptable carrier. The personal care composition may be in the form of an emulsion having an aqueous phase comprising water and an oil phase. The oil phase may comprise the isosorbide diester and a solid UV active soluble in the isosorbide diester. In a particular embodiment, the solid UV soluble in the isosorbide diester UV active may be selected from 4-tert-butyl-4'-methoxy dibenzoylmethane, bis-ethylhexyloxyphenol methoxyphenyl triazine, and combinations thereof. Methods of making the aforementioned personal care compositions are disclosed.

27 Claims, No Drawings

PERSONAL CARE COMPOSITIONS WITH IMPROVED SOLUBILITY OF A SOLID UV ACTIVE

FIELD OF THE INVENTION

The present invention relates to personal care composition comprising an isosorbide diester as a solvent for a solid UV active.

BACKGROUND OF THE INVENTION

Many personal care compositions are formulated for use as sunscreen or to provide a secondary benefit of UV protection. UV actives are used to provide such compositions with UV absorption capability. Many of the more robust UV actives providing an absorption benefit over a broader range of the UV spectra are solid materials. These solid UV actives require solubilization to provide an effective and consumer acceptable composition. For example, solid UV actives such as butyl methoxydibenzoylmethane (i.e., avobenzone) and/or (2-hydroxy-4-methoxyphenyl)-phenylmethanonebenzophenone-3 (i.e., benzophenone-3) or triazine compounds such as bis-ethylhexyloxyphenol methoxyphenyl triazine (i.e., bemotrizinol) require a solvent to keep these actives in solution or emulsion and to prevent crystallization.

Several solvents previously have been used to solubilize solid UV actives. Fatty esters of carboxylic acid such as C12-C15 alkyl bezonate are well known solvents for solid UV actives. Esters of adipic acid such as diisopropyl adipate are another suitable class of solvents for solid UV actives. Amide oils are widely used class of solvents for solid UV actives and include ethyl N-acetyl-N-butylaminoproprionate, or, more preferably, isopropyl lauroyl sarcosinate. However, there still exists a need for alternative solvents for solid UV actives. In particular, a need exists for solvents that can solubilize the UV active while also providing one or more additional skin or hair care benefits.

SUMMARY OF THE INVENTION

A personal care composition may comprise an isosorbide diester having the formula:

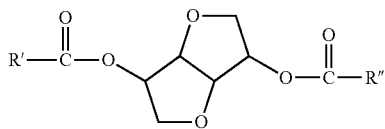

wherein R' and R" are independently selected from a straight or branched $C_{1-30}$ chain, which may be saturated or unsaturated. The composition may further comprise a solid UV active soluble in the isosorbide diester and a dermatologically acceptable carrier.

A personal care composition may be in the form of an emulsion comprising an aqueous phase comprising water and an oil phase. The oil phase may comprise an isosorbide diester having the formula presented above wherein R' and R" are independently selected from a straight or branched $C_{1-30}$ chain, which may be saturated or unsaturated. The oil phase may further comprise a solid UV active soluble in the isosorbide diester. In a particular embodiment, the solid UV soluble in the isosorbide diester UV active may be selected from 4-tert-butyl-4'-methoxy dibenzoylmethane, bis-ethylhexyloxyphenol methoxyphenyl triazine, and combinations thereof.

Methods of making the aforementioned personal care compositions are disclosed.

DETAILED DESCRIPTION OF THE INVENTION

The personal care composition of the present invention may be used in skin care, cosmetic, and hair care products, non-limiting uses of which include moisturizers, conditioners, anti-aging compounds, skin lightening compounds, and combinations thereof. The composition is applied to keratinous tissue of the face, neck, hands, arms and other areas of the body exposed to ultraviolet radiation.

In all embodiments of the present invention, all percentages are by weight of the personal care composition, unless otherwise specified. All ratios are weight ratios, unless specifically stated otherwise. All numeric ranges are inclusive of narrower ranges. The number of significant digits conveys neither limitation on the indicated amounts nor on the accuracy of the measurements. All measurements are understood to be made at ambient conditions, where "ambient conditions" means conditions at about 25° C., under about one atmosphere of pressure, and at about 50% relative humidity.

"Personal care composition" means compositions suitable for topical application on mammalian keratinous tissue.

"Keratinous tissue" refers to keratin-containing layers disposed as the outermost protective covering of mammals which includes, but is not limited to, skin, hair, nails, cuticles, etc.

"Stable" and "stability" refer to compositions which are substantially unaltered in chemical state, physical homogeneity and/or color, upon exposure to conditions reasonably expected to be incurred in shipping, storage and use, for example, for at least 30 days at a temperature of from about 0° C. to about 40° C.

"Derivative" refers to a molecule similar to that of another one, but differing from it in respect of a certain functional moiety. Derivatives may be formed by known reactive pathways. Suitable functional moieties include esters, ethers, amides, amines, carboxylic acids, hydroxyls, halogens, thiols, and/or salt derivatives of the relevant molecule.

"Substituted" means comprising at least one heteroatomic substituent. Non-limiting examples of substituents include atoms, such as oxygen atoms and nitrogen atoms, as well as functional groups, such as hydroxyl groups, ether groups, alkoxy groups, acyloxyalkyl groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups.

"Water-insoluble" means that less than about 0.01 g of solute dissolves in 100 ml of water, at 25° C. and 1 atm of pressure and neutral pH.

The term "apply" or "application," as used in reference to a composition, means to apply or spread the compositions of the present invention onto a keratinous tissue surface.

"Dermatologically acceptable" means that the compositions or components described are suitable for use in contact with keratinous tissue, such as human skin tissue, without undue toxicity, incompatibility, instability, allergic response, and the like.

The term "leave-on," in reference to compositions, means a composition intended to be applied to and allowed to remain on the keratinous tissue. These leave-on compositions are to be distinguished from compositions which are applied to the skin and subsequently (in a few minutes or less) removed either by washing, rinsing, wiping, or the like. Leave-on compositions exclude rinse-off applications such as shampoos, facial cleansers, hand cleansers, body wash, or body cleansers. The leave-on compositions may be substantially free of cleansing or detersive surfactants. For example, "leave-on compositions" may be left on the keratinous tissue for at least 15 minutes. For example, leave-on compositions may comprise less than 1% cleansing surfactants, less than 0.5% cleansing surfactants, or 0% cleansing surfactants. The compositions may, however, contain emulsifying or other processing surfactants that are not intended to provide any significant cleansing benefits when applied topically to the skin I. Personal Care Composition The present invention relates, in part, to personal care compositions comprising an isosorbide diester and a solid UV active soluble in the isosorbide diester. It has been surprisingly found that the isosorbide diesters are suitable solvents for certain solid UV actives. The isosorbide diesters perform as well or better than many convention solvents widely used with solid UV actives in select examples.

A. Form

The personal care composition may be a skin care, antiperspirant, deodorant, cosmetic, and hair care product. The personal care composition may be primarily used as a sunscreen. The personal care composition may have a primary use aside from being a sunscreen, which may include a moisturizer, conditioner, anti-aging compound, skin lightener, sunless tanner, anti-perspirant, shave preparation, aftershave, foundation, lipstick, hair styling product, shampoo, cleanser, and combinations thereof. In the aforementioned compositions, the sun-protection is a secondary function of the composition.

The personal care composition may involve a wide variety of forms. Non-limiting examples include simple solutions (e.g., water or oil based), dispersions, and emulsions. The personal care composition may be substantially anhydrous. "Substantially anhydrous" means that the composition comprises no more than about 1%, 0.5%, or, 0% water. The personal care compositions may be fluid or solid (gels, sticks, flowable solids, amorphous materials). In certain embodiments, the personal care composition is in the form of an emulsion. Emulsion may be generally classified as having a continuous aqueous phase (e.g., oil-in-water and water-in-oil-in-water) or a continuous oil phase (e.g., water-in-oil and oil-in-water-in-oil).

B. Isosorbide Diester

The personal care composition comprises an isosorbide diester. The isosorbide diester may have the following formula [I]:

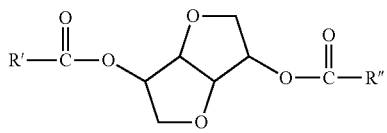

wherein R' and R" are independently selected from a straight or branched $C_{1-30}$ hydrocarbon chain, which may be saturated or unsaturated and which may be substituted. In one embodiment, R' and R" are independently selected from a straight or branched $C_{1-10}$ hydrocarbon chain, which may be saturated or unsaturated and which may be substituted. In certain embodiments, R' and R" are independently selected from a straight or branched $C_{1-30}$ or $C_{1-10}$ hydrocarbon chain, which may be saturated or unsaturated. In certain embodiments, R' and R" are independently selected from a straight or branched $C_{1-30}$ or $C_{1-10}$ hydrocarbon chain, which may be saturated. In other embodiments, R' and R" are a saturated, straight or branched $C_7$ chain. This particular embodiment has the INCI name of isosorbide dicaprylate. Isosorbide diesters of Formula I can be synthesized by know esterification techniques. For example, an isosorbide may be reacted with carboxylic acid having the desired R' or R" groups in the presence of basic or acidic catalysts under elevated pressure (100-500 kPa) and ideally elevated temperatures, for example of 120 to 220° C. Isolation may be performed by standard fractionation techniques. The isosorbide diesters may be more referred to as isosorbide diesters, In another embodiment, the personal care composition comprises an isosorbide diester that may have the following formula [II]:

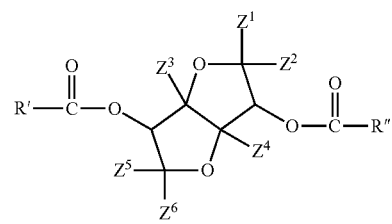

wherein R' and R" are independently selected from a straight or branched $C_{1-30}$ hydrocarbon chain, which may be saturated or unsaturated and which may be substituted; and wherein $Z^{1-6}$ are independently selected from hydrogen, hydroxyl, amino, amido, R', or R". In one embodiment, at least one of $Z^{1-6}$ is a hydroxyl group. In an alternate embodiment, $Z^1$, $Z^2$, $Z^5$, and $Z^6$ are independently selected from hydrogen, hydroxyl, amino, amido, R', or R"; and $Z^3$ and $Z^4$ are hydrogen.

The personal care composition may comprise a sufficient amount of the isosorbide diester to solubilize the solid UV active, which is described in further detail below. In certain embodiments, the personal care composition comprises at least 2 parts, by weight, isosorbide diester to solubilize every 1 part, by weight, solid UV active. In another embodiment, the personal care composition comprises at least 3 parts, 5 parts, or 8 parts, by weight, isosorbide diester to solubilize every 1 part, by weight, solid UV active. In yet another embodiment, the personal care composition comprises at least 10 parts, by weight, isosorbide diester to solubilize every 1 part, by weight, solid UV active. In select embodiments, the personal care composition may comprise from about 0.1% to about 95% of the isosorbide diester. For example, the personal care composition may comprise 0.1%, 0.5%, 1%, 2%, 5%, 10%, 15%, 20%, 25%, 30%, 35%, 40%, 45%, 50%, 55%, 60%, 65%, 70%, 75%, 80%, or 85%, to about 90%, 85%, 80%, 75%, 70%, 65%, 60%, 55%, 50%, 45%, 40%, 35%, 30%, 25%, 20%, 15%, 10%, 5%, or 3% of the isosorbide diester.

C. Solid UV Active

The personal care composition comprises at least one solid (at ambient conditions), UV active soluble in the isosorbide diester. The UV active is solid at ambient conditions. The solid UV actives may be an organic molecule (i.e., excluding inorganic UV actives such as titanium dioxide and zinc oxide). The solid UV active may be water-insoluble (i.e., excluding hydrophilic actives such as 2-phenylbenzimidazole-5-sulfonic acid or terephthalylidene dicamphor sulfonic acid). In order to deliver the solid UV active to keratinous tissue, the solid UV active may be substantially or fully dissolved, and, thus, does not remain in a solid or crystalline form in the personal care composition.

Suitable solid UV actives include dibenzoylmethane derivatives such as 4-tert-butyl-4'-methoxy dibenzoylmethane (i.e., butyl methoxydibenzoylmethane or avobenzone)(commercially available as PARSOL® 1789 from DSM). Other suitable solid UV actives include bis-ethylhexyloxyphenol methoxyphenyl triazine (i.e., bemotrizinol, commercially available as Tinosorb® S from BASF), 2,4,6-trianilino-(p-carbo-2'-ethylhexyl-1'-oxy)-1,3,5-tri azine (i.e., ethylhexyl triazone commercially available as Uvinul® T 150 from BASF), diethylhexyl butamido triazone (i.e., Iscotrizinol, commercially available as Uvasorb® HEB by 3V Sigma), diethylamino hydroxybenzoyl hexyl benzoate (commercially available as Uvinul® A Plus from BASF), benzophenone-3 (i.e., (2-Hydroxy-4-methoxyphenyl)-phenylmethanone or oxybenzone, available Eusolex 4360 from EMD Chemical, Inc.), 4-methylbenzylidene camphor (commercially available as PARSOL® 5000 from DSM), ethylhexyl bis-isopentylbenzoxazolylphenyl melamine (commercially available as Uvasorb® k2A by 3V Sigma), and combinations thereof.

In certain embodiments, the solid UV active is selected from 4-tert-butyl-4'-methoxy dibenzoylmethane, bis-ethylhexyloxyphenol methoxyphenyl triazine, and combinations thereof.

The personal care composition may comprise an amount of the solid UV active to provide a desired UV absorption or sunscreen benefit. The personal care composition may comprise an amount of the solid UV active as prescribed or proposed by regulatory agencies in the US (e.g., 21 CFR part 352, 68 Federal Register 41386, 70 Federal Register 72449, or 71 Federal Register 42405), Europe (Regulation No 1223/2009 of the EU Parliament; Annex VI), Japan, China, Australia, New Zealand, or Canada. In particular embodiments, the personal care composition comprises from about 0.01% to about 20%, by weight of the composition, of a solid UV active. In other embodiments, the personal care composition comprises from about 0.1%, 0.5%, or 1% to about 15%, 10%, 6%, 5%, or 3%, by weight of the composition, of a solid UV active. In another embodiment, the personal care composition may comprise a sufficient about of solid UV active to yield a Sun Protection Factor of at least about 15, 30 45, or 50. SPF testing is conventional and well understood in the art. A suitable SPF test is prescribed in 21 C.F.R. 352, Subpart D. In other embodiments, the personal care composition may comprise a sufficient about of solid UV active to yield a UVA protection value of low, medium, high, or, ideally, highest, as defined by the U.S. Federal Drug Administration in sections 352.71-73 in the proposed rule published in 72 Federal Register 49070 on Aug. 27, 2007.

D. Carrier

The personal care composition may comprise a one or more carriers. Carriers may be selected for various stability, aesthetics, and/or compatibility with other materials present in the personal care composition.

Suitable carriers include water and/or water miscible solvents. The personal care composition may comprise from about 1% to about 95% by weight of water and/or water miscible solvent. The composition may comprise from about 1%, 3%, 5%, 10%, 15%, 20%, 25%, 30%, 35%, 40%, 45%, 50%, 55%, 60%, 65%, 70%, 75%, 80%, or 85% to about 90%, 85%, 80%, 75%, 70%, 65%, 60%, 55%, 50%, 45%, 40%, 35%, 30%, 25%, 20%, 15%, 10%, or 5% water and/or water miscible solvents. Suitable water miscible solvents include monohydric alcohols, dihydric alcohols, polyhydric alcohols, glycerol, glycols, polyalkylene glycols such as polyethylene glycol, and mixtures thereof. Particularly suitable solvents, include lower aliphatic alcohols such as ethanol, propanol, butanol, isopropanol; diols such as 1,2-propanediol,1,3-propanediol, butanediol, pentanediol, hexanediol, heptanediol, decanediol; glycerin; water, and mixtures thereof. In certain embodiments, the personal care composition comprises water, diols, glycerin, and combinations thereof. When the personal care product is in the form of an emulsion, water and/or water miscible solvents are carriers typically associated with the aqueous phase.

Suitable carriers also include oils. The personal care composition may comprise from about 1% to about 95% by weight of one or more oils. The composition may comprise from about 0.1%, 0.5%, 1%, 2%, 5%, 10%, 15%, 20%, 25%, 30%, 35%, 40%, 45%, 50%, 55%, 60%, 65%, 70%, 75%, 80%, 85%, or 90% to about 90%, 85%, 80%, 75%, 70%, 65%, 60%, 55%, 50%, 45%, 40%, 35%, 30%, 25%, 20%, 15%, 10%, 5%, or 3% of one or more oils. Oils may be used to solubilize, disperse, or carry materials that are not suitable for water or water soluble solvents. Suitable oils include silicones, hydrocarbons, esters, amides, ethers, and mixtures thereof. Oils may be fluid at room temperature. However, certain personal care product forms (i.e., solid or semi-solid stick) may require non-fluid oils. The oils may be volatile or nonvolatile. "Non-volatile" means a material that exhibit a vapor pressure of no more than about 0.2 mm Hg at 25° C. at one atmosphere and/or a material that has a boiling point at one atmosphere of at least about 300° C. "Volatile" means that the material exhibits a vapor pressure of at least about 0.2 mm of mercury at 20° C. Volatile oils may be used to provide a lighter feel when a heavy, greasy film is undesirable. When the personal care product is in the form of an emulsion, oils are carriers typically associated with the oil phase.

Suitable oils include volatile oils. In certain embodiments, the volatile oils may have a viscosity ranging from about 0.5 to 5 centistokes at 25° C. Volatile oils may be used to promote more rapid drying of the skin care composition after it is applied to skin. Nonvolatile oils are also suitable for use in the composition. Nonvolatile oils are often used for emolliency and protective properties.

Suitable silicone oils include polysiloxanes. Polylsiloxanes may have a viscosity of from about 0.5 to about 1,000,000 centistokes at 25° C. Such polysiloxanes can be represented by the general chemical formula:

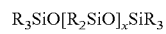

wherein R is independently selected from hydrogen or $C_{1-30}$ straight or branched chain, saturated or unsaturated alkyl, phenyl or aryl, trialkylsiloxy; and x is an integer from 0 to about 10,000, chosen to achieve the desired molecular. In certain embodiments, R is hydrogen, methyl, or ethyl. Commercially available polysiloxanes include the polydimethylsiloxanes, which are also known as dimethicones, examples of which include the DM-Fluid series from Shin-Etsu, the Vicasil® series sold by Momentive Performance Materials Inc., and the Dow Corning® 200 series sold by Dow Corning Corporation. Specific examples of suitable polydimethylsiloxanes include Dow Corning® 200 fluids (also sold as Xiameter® PMX-200 Silicone Fluids) having viscosities of 0.65, 1.5, 50, 100, 350, 10,000, 12,500 100,000, and 300,000 centistokes.

Suitable dimethicones include those represented by the chemical formula:

wherein R and R' are each independently hydrogen or $C_{1-30}$ straight or branched chain, saturated or unsaturated alkyl, aryl, or trialkylsiloxy; and x and y are each integers of 1 to 1,000,000 selected to achieve the desired molecular weight. Suitable silicones include phenyl dimethicone (Botansil™ PD-151 from Botanigenics, Inc.), diphenyl dimethicone (KF-53 and KF-54 from Shin-Etsu), phenyl trimethicone (556 Cosmetic Grade Fluid from Dow Corning), or trimethylsiloxyphenyl dimethicone (PDM-20, PDM-200, or PDM-1000 from Wacker-Belsil). Other examples include alkyl dimethicones wherein at least R' is a fatty alkyl (e.g., $C_{12-22}$). A suitable alkyl dimethicone is cetyl dimethicone, wherein R' is a straight C16 chain and R is methyl. Cetyl dimethicone, is available as s 2502 Cosmetic Fluid from Dow Corning or as Abil Wax 9801 or 9814 from Evonik Goldschmidt GmbH.

Cyclic silicones are one type of silicone oil that may be used in the composition. Such silicones have the general formula:

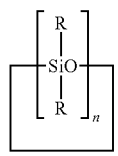

wherein R is independently selected from hydrogen or $C_{1-30}$ straight or branched chain, saturated or unsaturated alkyl, phenyl or aryl, trialkylsiloxy; and where n=3-8 and mixtures thereof. Commonly, a mixture of cyclomethicones is used where n is 4, 5, and/or 6. Commercially available cyclomethicones include Dow Corning UP-1001 Ultra Pure Fluid (i.e. n=4), Dow Corning XIAMETER® PMX-0245 (i.e. n=5), Dow Corning XIAMETER® PMX-0245 (i.e. n=6), Dow Corning 245 fluid (i.e. n=4 and 5), and Dow Corning 345 fluid (i.e. n=4, 5, and 6).

Suitable hydrocarbon oils include straight, branched, or cyclic alkanes and alkenes. The chain length may be selected based on desired functional characteristics such as volatility. Suitable volatile hydrocarbons may have between 5-20 carbon atoms or, alternately, between 8-16 carbon atoms.

Other suitable oils include esters. The suitable esters typically contained at least 10 carbon atoms. These esters include esters with hydrocarbyl chains derived from fatty acids or alcohols (e.g., mono-esters, polyhydric alcohol esters, and di- and tri-carboxylic acid esters). The hydrocarbyl radicals of the esters hereof may include or have covalently bonded thereto other compatible functionalities, such as amides and alkoxy moieties (e.g., ethoxy or ether linkages, etc.). Exemplary esters include, but are not limited to, isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, C12-15 alkyl benzoate, diisopropyl adipate, dibutyl adipate, and oleyl adipate. Other suitable esters are further described in the Personal Care Product Council's *International Cosmetic Ingredient Dictionary and Handbook*, Thirteenth Edition, 2010, under the functional category of "Esters." Other esters suitable for use in the personal care composition include those known as polyhydric alcohol esters and glycerides.

Other suitable oils include amides. Amides include compounds having an amide functional group while being liquid at 25° C. and insoluble in water. Suitable amides include N-acetyl-N-butylaminopropionate, isopropyl N-lauroylsarcosinate, and N,N-diethyltoluamide. Other suitable amides are disclosed in U.S. Pat. No. 6,872,401.

Other suitable oils include ethers. Suitable ethers include saturated and unsaturated fatty ethers of a polyhydric alcohol, and alkoxylated derivatives thereof. Exemplary ethers include $C_{4-20}$ alkyl ethers of polypropylene glycols, and di-$C_{8-30}$ alkyl ethers. Suitable examples of these materials include PPG-14 butyl ether, PPG-15 stearyl ether, dioctyl ether, dodecyl octyl ether, and mixtures thereof.

The personal care composition may comprise an emulsifier. An emulsifier is particularly suitable when the composition is in the form of an emulsion or if immiscible materials are being combined. The skin care composition may comprise from about 0.05%, 0.1%, 0.2%, 0.3%, 0.5%, or 1% to about 20%, 10%, 5%, 3%, 2%, or 1% emulsifier. Emulsifiers may be nonionic, anionic or cationic. Non-limiting examples of emulsifiers are disclosed in U.S. Pat. No. 3,755,560, U.S. Pat. No. 4,421,769, and McCutcheon's, *Emulsifiers and Detergents*, 2010 Annual Ed., published by M. C. Publishing Co. Other suitable emulsifiers are further described in the Personal Care Product Council's *International Cosmetic Ingredient Dictionary and Handbook*, Thirteenth Edition, 2006, under the functional category of "Surfactants—Emulsifying Agents."

Suitable emulsifiers include the following classes of ethers and esters: ethers of polyglycols and of fatty alcohols, esters of polyglycols and of fatty acids, ethers of polyglycols and of fatty alcohols which are glycosylated, esters of polyglycols and of fatty acids which are glycosylated, ethers of $C_{12-30}$ alcohols and of glycerol or of polyglycerol, esters of $C_{12-30}$ fatty acids and of glycerol or of polyglycerol, ethers of oxyalkylene-modified $C_{12-30}$ alcohols and of glycerol or polyglycerol, ethers of $C_{12-30}$ fatty alcohols comprising and of sucrose or of glucose, esters of sucrose and of $C_{12-30}$ fatty acids, esters of pentaerythritol and of $C_{12-30}$ fatty acids, esters of sorbitol and/or of sorbitan and of $C_{12-30}$ fatty acids, ethers of sorbitol and/or of sorbitan and of alkoxylated sorbitan, ethers of polyglycols and of cholesterol, esters of $C_{12-30}$ fatty acids and of alkoxylated ethers of sorbitol and/or sorbitan, and combinations thereof.

Linear or branched type silicone emulsifiers may also be used. Particularly useful polyether modified silicones include KF-6011, KF-6012, KF-6013, KF-6015, KF-6015, KF-6017, KF-6043, KF-6028, and KF-6038 from Shin Etsu. Also particularly useful are the polyglycerolated linear or branched siloxane emulsifiers including KF-6100, KF-6104, and KF-6105 from Shin Etsu.

Emulsifiers also include emulsifying silicone elastomers. Suitable emulsifying silicone elastomers may include at least one polyalkyl ether or polyglycerolated unit. Polyoxyalylenated emulsifying silicone elastomers that may be used in at least one embodiment of the invention include those sold by Shin-Etsu Silicones under the names KSG-21, KSG-20, KSG-30, KSG-31, KSG-32, KSG-33; KSG-210 (dimethicone/PEG-10/15 crosspolymer dispersed in dimethicone); KSG-310 (PEG-15 lauryl dimethicone crosspolymer); KSG-320 (PEG-15 lauryl dimethicone crosspolymer dispersed in isododecane); KSG-330 (PEG-15 lauryl dimethicone crosspolymer dispersed in triethylhexanoin), KSG-340 (PEG-10 lauryl dimethicone crosspolymer and PEG-15 lauryl dimethicone crosspolymer). Other silicone emulsifying elastomers are supplied by Dow Corning™, including PEG-12 dimethicone crosspolymers (DC 9010 and 9011). Other suitable silicone emulsifiers sold by Dow Corning include DC9010 and DC9011. Polyglycerolated emulsifying silicone elastomers are disclosed in PCT/WO 2004/024798. Such elastomers include Shin-Etsu's KSG series, such as KSG-710 (dimethicone/polyglycerin-3 crosspolymer dispersed in dimethicone); or lauryl dimethicone/polyglycerin-3 crosspolymer dispersed in a variety of solvent such as isododecane, dimethicone, triethylhexanoin, available as KSG-810, KSG-820, KSG-830, or KSG-840 from Shin-Etsu.

Structuring agents may be used to increase viscosity, thicken, solidify, or provide solid or crystalline structure to the personal care composition. Structuring agents are typically grouped based on solubility, dispersibility, or phase compatibility. Examples of aqueous or water structuring agents include polymeric agents, natural or synthetic gums, polysaccharides, and the like. In one embodiment, the composition may comprises from about 0.0001%, 0.001%, 0.01%, 0.05%, 0.1%, 0.5%, 1%, 2%, 3%, 5% to about 25%, 20%, 10%, 7%, 5%, 4%, or 2%, by weight of the composition, of one or more structuring agents.

Polysaccharides and gums may be suitable aqueous phase thickening agents. Suitable classes of polymeric structuring agents include but are not limited to carboxylic acid polymers, polyacrylamide polymers, sulfonated polymers, high molecular weight polyalkylglycols or polyglycerins, copolymers thereof, hydrophobically modified derivatives thereof, and mixtures thereof.

Examples of oil structuring agents include silicone and organic based materials. Suitable ranges of oil structuring agents are from about 0.01%, 0.05%, 0.1% 0.5%, 1%, 2.5%, 5%, or 10% to about 30%, 25%, 20%, 15%, 10%, or 5%. Suitable oil phase structuring agents may be silicone based, such as silicone elastomers, silicone gums, silicone waxes, linear silicones having a degree of polymerization allowing the silicone to increase the viscosity of the oil phase. Examples of silicone structuring agents include, but are not limited to, silicone elastomers, silicone gums, and silicone waxes, Suitable silicone elastomers may be in the powder form, or dispersed or solubilized in solvents such as volatile or nonvolatile silicones, or silicone compatible vehicles such as paraffinic hydrocarbons or esters. Examples of silicone elastomer powders include vinyl dimethicone/methicone silsesquioxane crosspolymers like KSP-100, KSP-101, KSP-102, KSP-103, KSP-104, KSP-105, available from Shin-Etsu, hybrid silicone powders that contain a fluoroalkyl group like KSP-200, available from Shin-Etsu, which is a fluoro-silicone elastomer, and hybrid silicone powders that contain a phenyl group such as KSP-300, available from Shin-Etsu, which is a phenyl substituted silicone elastomer; and DC 9506 available from Dow Corning.

Examples of silicone elastomer dispersions include dimethicone/vinyl dimethicone crosspolymers supplied by a variety of suppliers including Dow Corning Corporation under the tradenames DC9040 or DC9041, Momentive under the tradename SFE 839, or Shin-Etsu Silicones under the tradenames KSG-15, 16, 18. KSG-15 has the INCI name cyclopentasiloxane (and) dimethicone/vinyl dimethicone crosspolymer. KSG-18 has the INCI name diphenylsiloxy phenyl trimethicone (and) dimethicone/phenyl vinyl dimethicone crossopolymer. Silicone elastomers may also be purchased from Grant Industries under the Gransil trademark. Other suitable silicone elastomers have long chain alkyl substitutions such as lauryl dimethicone/vinyl dimethicone crosspolymers supplied by Shin Etsu under the tradenames KSG-41, KSG-42, KSG-43, and KSG-44, wherein the elastomer is dispersed in solvents including mineral oil, isodocane, triethylhexanoin, or squalene, respectively. Other suitable silicone elastomers may have polyglycerine substitutions such as lauryl dimethicone/polyglycerin-3 crosspolymers supplied by Shin Etsu under the tradenames KSG-810, KSG-820, KSG-830, and KSG-840, wherein the elastomer is dispersed in solvents including mineral oil, isodocane, triethylhexanoin, or squalene, respectively. Other suitable silicone elastomers may have polyglycol substitutions such as PEG-15/lauryl dimethiconecrosspolymers supplied by Shin Etsu under the tradenames KSG-310, KSG-320, KSG-330, and KSG-340, wherein the elastomer is dispersed in solvents including mineral oil, isodocane, triethylhexanoin, or squalene, respectively. Other suitable silicone elastomers having polyglycol substitutions include Shin Etsu's KSG-210, a dimethicone/PEG-10/15 crosspolymer in dimethicone.

Silicone gums are another oil phase structuring agent. The silicone gum typically has a viscosity ranging from about 500,000 to 100 million cst at 25° C., from about 600,000 to 20 million, from about 600,000 to 12 million cst. Suitable silicone gums include those sold by Wacker-Belsil under the trade names CM3092, Wacker-Belsil 1000, or Wacker-Belsil DM 3096. A particularly suitable silicone gum is as dimethiconol, available from Dow Corning Corporation under the trade name 1-1254 Fluid, 2-9023 Fluid, and 2-9026 Fluid. Dimethiconol is often sold as a mixture with a volatile or nonvolatile silicone such as Dow Corning 1401 Fluid, 1403 Fluid, and 1501 Fluid.

Another type of oily phase structuring agent includes silicone waxes. Silicone waxes may be referred to as alkyl silicone waxes which and are semi-solids or solids at room temperature. The term "alkyl silicone wax" means a polydimethylsiloxane having a substituted long chain alkyl (such as C16 to 30) that confers a semi-solid or solid property to the siloxane. Examples of such silicone waxes include stearyl dimethicone, which may be purchased from Evonik Goldschmidt GmbH under the tradename Abil Wax 9800 or from Dow Corning under the tradename 2503. Another example is bis-stearyl dimethicone (which may be purchased from Gransil Industries under the tradename Gransil A-18), behenyl dimethicone, or behenoxy dimethicone.

Other suitable viscosity increasing agents include polyamides and polysilicone-polyamide copolymers. Suitable polysilicone-polyamide copolymers are disclosed in U.S. Patent Application Publication No. 2004/0170586.

Other oil phase structuring agent may be one or more natural or synthetic waxes such as animal, vegetable, or mineral waxes. Suitable silicone waxes are disclosed in U.S. Pat. Nos. 5,413,781 and 5,725,845, and further include alkylmethyl polysiloxanes, C10-C60 alkyl dimethicones, and mixtures thereof.

Other structuring agents include natural or synthetic montmorillonite minerals, silicas, silicates, silica silylate, and alkali metal or alkaline earth metal derivatives thereof.

Optional Ingredients

The personal care composition may comprise one or more optional ingredients.

A. Photostabilizers—The personal care composition may comprise a photostabilizer. The composition may comprise from about 0.0001%, 0.001%, 0.01%, 0.05%, 0.1%, 0.5%, or 1% to about 20%, 10%, 7%, or 5%, by weight of the composition, of one or more suitable photostabilizer.

A suitable photostabilizer is alpha-cyanodiphenylacrylate is as disclosed in U.S. Pat. No. 7,713,519. The alpha-cyanodiphenylacrylate may have the general formula:

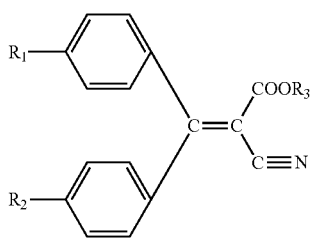

wherein one or both of R1 and R2 is independently a straight or branched chain C1-30 alkoxy radical and any non-alkoxy R1 or R2 radical is hydrogen; and R3 is a straight or branched chain C1-30 alkyl. Alternately, one or both of R1 and R2 is independently a C1-8 alkoxy radical and any non-alkoxy R1 or R2 radical is hydrogen; and R3 is a straight of branched chain C2-20 alkyl. Alternately, one or both of R1 and R2 is independently methoxy, and any non-methoxy R1 or R2 is hydrogen; and R3 is a straight or branched chain C2-20 alkyl.

A suitable alpha-cyanodiphenylacrylate is ethylhexyl methoxycrylene, or 2-ethylhexyl 2-cyano-3-(4-methoxyphenyl)-3-phenylpropenoate, wherein R1 is methoxy, R2 is hydrogen, and R3 is 2-ethylhexyl. This material is available from Hallstar Company under trade name Solastay® 51.

Another suitable photostabilizer includes diesters or polyesters of naphthalene dicarboxylic acid as disclosed in U.S. Pat. Nos. 5,993,789, 6,113,931, 6,126,925 and 6,284,916. Suitable diesters or polyesters of naphthalene dicarboxylic acid may have the following formula:

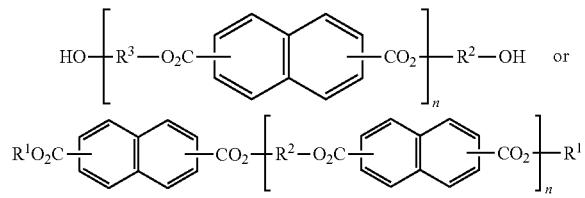

wherein each $R^1$ independently is an alkyl group having 1 to 22 carbon atoms, or a diol having the formula HO—$R^2$—OH, or a polyglycol having the formula HO—$R^3$—(—O—$R^2$—)$_m$—OH, and, wherein $R^2$ and $R^3$, same or different, are each an alkylene group, straight chain or branched, having 1 to 6 carbon atoms, wherein m and n are each 1 to about 100, 1 to about 10, or 2 to about 7. A suitable diester of naphthalene dicarboxylic acid is diethylhexyl 2,6-naphthalate available as Corapan® TQ from Symrise.

Another suitable photostabilizer is 4-hydroxybenzylidenemalonate derivatives or 4-hydroxycinnamate derivatives. Suitable materials may have the following formula:

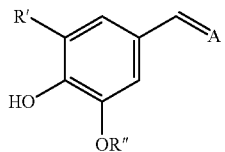

wherein A is a chromophoric group that absorbs UV-radiation, comprises one divalent group or two monovalent groups with at least one group having carbonyl (C=O) functionality; R' is hydrogen, a linear or branched $C_1$-$C_8$ alkyl radical or a linear or branched $C_1$-$C_8$ alkoxy radical; and R" is a linear or branched $C_1$-$C_8$ alkyl radical. Exemplary compounds include ethyl-alpha-cyano-3,5-dimethoxy-4-hydroxy cinnamate, ethyl-alpha-acetyl-3,5-dimethoxy-4-hydroxy cinnamate, iso-propyl-alpha-acetyl-3,5-dimethoxy-4-hydroxy cinnamate, iso-amyl-alpha-acetyl-3,5-dimethoxy-4-hydroxy cinnamate, 2-ethylhexyl-alpha-acetyl-3,5-dimethoxy-4-hydroxy cinnamate, diethyl-3,5-dimethoxy-4-hydroxy benzylidene malonate, di-(2-ethylhexyl)-3,5-dimethoxy-4-hydroxy benzylidene malonate, diisoamyl-3,5-dimethoxy-4-hydroxy benzylidene malonate, didodecyl-3,5-dimethoxy-4-hydroxy benzylidene malonate, dipalmitoyl-3,5-dimethoxy-4-hydroxy benzylidene malonate, and di-isopropyl-3,5-dimethoxy-4-hydroxy benzylidene malonate. A particularly suitable compound is diethylhexyl syringylidenemalonate (INCI name) available under the tradename Oxynex® ST from EMD Chemicals, Inc. Additional suitable 4-hydroxybenzylidenemalonate derivatives or 4-hydroxycinnamate derivatives are disclosed in U.S. Pat. No. 7,357,919 and U.S. Patent Application Publication No. 2003/0108492A1 and US2003/0157035A.

Other suitable photostabilizers include a 2-pyrrolidinone-4-carboxy ester compounds as described in U.S. Patent Application Publication No. 2010/0183529; silicon-containing s-triazines substituted with two aminobenzoate or aminobenzamide groups as described in U.S. Patent Application Publication No. 2008/0145324; fluorene derivatives as described in U.S. Patent Application Publications Nos. 2004/0057912, 2004/0057914, 2004/0057916, and 2004/062726; piperidinol salts as described in U.S. Patent Application Publications No. 2005/0220727 including tris(tetramethylhydroxypiperidinol) citrate sold under the tradename Tinogard® Q by Ciba; and arylalkyl amides and esters as described in U.S. Patent Application Publication No. 2008/0019930.

Other suitable photostabilizers are listed in the functional category of "Light Stabilizers" in the Personal Care Product Council's *International Cosmetic Ingredient Dictionary and Handbook*, Thirteenth Edition, 2010.

B. Additional UV Active—The personal care composition may comprise an additional UV active. "Additional UV active" means UV actives that are not solid or are not soluble in the isosorbide diester as described above. The personal care composition may comprise an amount of additional UV active to provide a desired UV absorption or sunscreen benefit. The composition may comprise from about 0.0001%, 0.001%, 0.01%, 0.05%, 0.1%, 0.5%, or 1% to about 20%, 10%, 7%, or 5%, by weight of the composition, of one or more suitable additional UV active. In another embodiment, the personal care composition may comprise a sufficient about of additional UV active to yield a Sun Protection Factor of at least about 15, 30 45, or 50. In other embodiments, the personal care composition may comprise a sufficient about of additional UV active to yield a UVA protection value of low, medium, high, or, ideally, highest.

Suitable additional UV actives include dibenzoylmethane compounds other than 4-tert-butyl-4'-methoxy dibenzoylmethane. Other suitable additional UV actives include 2-ethylhexyl-p-methoxycinnamate; octyldimethyl-p-aminobenzoic acid; 2-ethylhexyl-2-cyano-3,3-diphenylacrylate; 2-ethylhexyl salicylate; homomethyl salicylate; 2-phenylbenzimidazole-5-sulfonic acid; 2-(p-dimethylaminophenyl)-5-sulfonicbenzoxazoic acid; disodium phenyl dibenzimidazole tetrasulfonate; sodium dihydroxy dimethoxy disulfobenzophenone; polysilicone-15; isoamyl p-methoxycinnamate; and combinations thereof. Suitable additional UV actives include inorganic particulates such as zinc oxide and titanium dioxide and organic particulates such as methylene bis-benzotriazolyl tetramethylbutylphenol (commercially available as Tinosorb® M from BASF).

In one embodiment, the personal care composition comprises at least 1 part, by weight, of an additional UV active to every 1 part, by weight, of the solid UV active. In a particular embodiment, the personal care composition comprises at least 1 part, by weight, of 2-ethylhexyl-2-cyano-3,3-diphenylacrylate to every 1 part, by weight, of the solid UV active. In a select embodiment, the personal care composition comprises at least 1 part, by weight, of 2-ethylhexyl-2-cyano-3,3-diphenylacrylate to every 1 part, by weight, of the solid UV active, wherein the solid UV active is 4-tert-butyl-4'-methoxy dibenzoylmethane.

C. Skin Care Actives—The personal care compositions may comprise one or more optional components to provide an efficacious and/or consumer desirable product. For example, the composition can include other actives or agents. For instance, suitable optional actives and agents may include an active or agent selected from a group consisting of sugar amines, vitamins, oil control agents, photosterols, hexamidine compounds, tightening agents, anti-wrinkle actives, anti-atrophy actives, flavonoids, N-acyl amino acid compounds, retinoids, peptides, particulate materials, UV actives, photostabilizers, anti-cellulite agents, desquamation actives, anti-acne actives, anti-oxidants, radical scavengers, conditioning agents, anti-inflammatory agents, tanning actives, skin lightening agents, botanical extracts, antimicrobial actives, antifungal actives, antibacterial actives, antiperspirant actives, sensates, preservatives, anti-dandruff actives, detersive surfactants, and combinations thereof. Examples of these materials are provided in U.S. Patent Application Publication No. US2007/0185038A1, US2006/0275237A1, US2004/0175347A1, and US2006/0263309A1. The personal care composition may comprise from about 0.0001%, 0.001%, 0.01%, 0.05%, 0.1%, 0.5%, 1%, 2%, or 3% to about 30%, 25%, 20%, 15%, 10%, 7%, 5%, 3%, 2%, or 1%, by weight of the composition, of one or more skin care actives.

In certain embodiments, skin care actives may be selected from sugar amines, vitamins, hexamidine compounds, peptides, flavonoids, hydroxy acids, phytosterols, glycyrrhetinic acid, and combinations thereof.

Examples of sugar amines that are useful herein include glucosamine, N-acetyl glucosamine, mannosamine, N-acetyl mannosamine, galactosamine, N-acetyl galactosamine, their isomers (e.g., stereoisomers), and their salts (e.g., HCl salt). Preferred for use herein are glucosamine, particularly D-glucosamine and N-acetyl glucosamine, particularly N-acetyl-D-glucos amine.

"Vitamins" means vitamins, pro-vitamins, and their salts, isomers and derivatives. Non-limiting examples of suitable vitamins include: vitamin B compounds (including B1 compounds, B2 compounds, B3 compound, B5 compounds, such as panthenol or "pro-B5", pantothenic acid, pantothenyl; B6 compounds, such as pyroxidine, pyridoxal, pyridoxamine; carnitine, thiamine, riboflavin); vitamin A compounds, and all natural and/or synthetic analogs of Vitamin A, including retinoids, retinol, retinyl acetate, retinyl palmitate, retinoic acid, retinaldehyde, retinyl propionate, carotenoids (pro-vitamin A), and other compounds which possess the biological activity of Vitamin A; vitamin D compounds; vitamin K compounds; vitamin E compounds, or tocopherol, including tocopherol sorbate, tocopherol acetate, tocopherol succinate, other esters of tocopherol and tocopheryl compounds; vitamin C compounds, including ascorbate, ascorbyl esters of fatty acids, and ascorbic acid derivatives, for example, ascorbyl phosphates such as magnesium ascorbyl phosphate and sodium ascorbyl phosphate, ascorbyl glucoside, and ascorbyl sorbate; and vitamin F compounds, such as saturated and/or unsaturated fatty acids.

In certain embodiments, the personal care compositions comprise a vitamin B3 compound. As used herein, "vitamin B3 compound" means a compound having the formula:

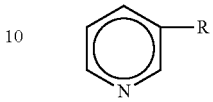

wherein R is —CONH$_2$ (i.e., niacinamide), —COOH (i.e., nicotinic acid) or —CH2OH (i.e., nicotinyl alcohol); derivatives thereof; and salts of any of the foregoing.

The personal care compositions may include hexamidine compounds, its salts, and derivatives. As used herein, "hexamidine compound" means a compound having the formula:

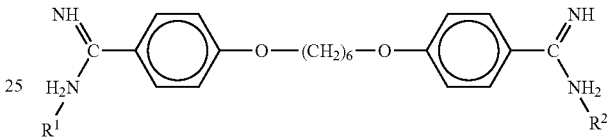

wherein R$^1$ and R$^2$ are optional or are organic acids (e.g., sulfonic acids, etc.) A suitable hexamidine compounds includes hexamidine diisethionate, commercially available as Eleastab® HP100 from Laboratoires Serobiologiques.

As used herein, "peptide" refers to peptides containing ten or fewer amino acids and their derivatives, isomers, and complexes with other species such as metal ions (e.g., copper, zinc, manganese, magnesium, and the like). Peptide refers to both naturally occurring and synthesized peptides. Also useful herein are naturally occurring and commercially available compositions that contain peptides. The peptides may contain at least one basic amino acid (e.g., histidine, lysine, arginine). For example, suitable peptides are the dipeptide carnosine (beta-ala-his), the tripeptide gly-his-lys, the tripeptide his-gly-gly, the tripeptide gly-gly-his, the tripeptide gly-his-gly, the tetrapeptide gly-gln-pro-arg, the pentapeptide lys-thr-thr-lys-ser, lipophilic derivatives of peptides, and metal complexes of the aforementioned (e.g., copper complex of the tripeptide his-gly-gly (also known as Iamin)). Other suitable peptides include Peptide CK (arg-lys-arg); Peptide CK+ (ac-arg-lys-arg-NH$_2$); and Peptide E, arg-ser-arg-lys. A commercially available tripeptide derivative-containing composition is Biopeptide CL® (from Sederma, France), which contains 100 ppm of palmitoyl-gly-his-lys and is commercially available. A commercially available pentapeptide derivative-containing composition is Matrixyl® (from Sederma, France), which contains 100 ppm of palmitoyl-lys-thr-thr-lys-ser. A suitable peptide is a dipeptide based molecule having a C terminal amino acid of threonine, such as plamitoyl-lys-thr, as described in US Patent Application Publication 2007/0020220 A1.

Peptide derivatives useful herein include lipophilic derivatives such as palmitoyl derivatives. In one embodiment, the peptide is selected from palmitoyl-lys-thr-thr-lys-ser, palmitoyl-gly-his-lys, their derivatives, and combinations thereof.

Polyphenolic compounds include flavonoids such as those broadly disclosed in U.S. Pat. No. 5,686,082. Exemplary flavonoids include one or more flavones, one or more isoflavones, one or more coumarins, one or more chromones, one or more dicoumarols, one or more chromanones, one or more chromanols, isomers (e.g., cis/trans isomers) thereof, and mixtures thereof. Suitable flavones and isoflavones include unsubstituted flavone, unsubstituted isoflavone, daidzein (7,4'-dihydroxy isoflavone), genistein (5,7,4'-trihydroxy isoflavone), equol (7,4'-dihydroxy isoflavan), 5,7-dihydroxy-4'-methoxy isoflavone, 7,2'-dihydroxy flavone, 3',4'-dihydroxy naphthoflavone, 7,8-benzoflavone, 4'-hydroxy flavone, 5,6-benzoflavone, soy isoflavones (e.g., isoflavones extracted from soy) and other plant sources of such mixtures (e.g., red clover), and mixtures thereof. Other suitable flavonoids include hesperitin, hesperidin, and mixtures thereof. Other polyphenolic compounds include hexylresorcinol and tetrahydrocurcuminoids including tetrahydrocurcumin (i.e., INIC name tetrahydrodiferuloylmethane), tetrahydrodemethoxycurcumin (i.e., INIC name tetrahydrodemethoxydiferuloylmethan), and tetrahydrobismethoxycurcumin (i.e., INCI name tetrahydrobisdemethoxydiferuloylmethane).

Hydroxy acids include alpha- and beta-hydroxy acids. Suitable alpha-hydroxy acids include including glycolic acid, lactic acid, malic acid, citric acid, tartaric acid, and derivatives thereof. Suitable beta-hydroxy acids include salicylic acid, carnitine, and derivatives thereof.

The topical compositions of the present invention can comprise one or more N-acyl amino acid compounds. The amino acid can be one of any of the amino acids known in the art. The N-acyl amino acid compounds of the present invention can correspond to the formula:

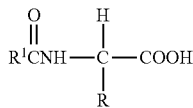

wherein R can be a hydrogen, alkyl (substituted or unsubstituted, branched or straight chain), or a combination of alkyl and aromatic groups. $R^1$ can be $C_1$ to $C_{30}$, saturated or unsaturated, straight or branched, substituted or unsubstituted alkyls; substituted or unsubstituted aromatic groups; or mixtures thereof. In certain embodiments, the N-acyl amino acid compound is selected from the group consisting of N-acyl phenylalanine, N-acyl tyrosine, their isomers, their salts, and derivatives thereof. The amino acid can be the D or L isomer or a mixture thereof. An exemplary N-acyl amino acid is N-undecylenoyl-L-phenylalanine, wherein the acyl group is a C11 mono-unsaturated fatty acid moiety and the amino acid is the L-isomer of phenylalanine. N-undecylenoyl-L-phenylalanine is commercially available under the tradename Sepiwhite® from SEPPIC.

Phytosterols can be synthetic or natural in origin and can be used as essentially pure compounds or mixtures of compounds (e.g., extracts from natural sources). Phytosterols are generally found in the unsaponifiable portion of vegetable oils and fats and are available as free sterols, acetylated derivatives, sterol esters, ethoxylated or glycosidic derivatives. Exemplary phytosterols include beta-sitosterol, campesterol, brassicasterol, delta-5-avennasterol, lupenol, alpha-spinasterol, stigmasterol, their derivatives, isomers, tautomers, and combinations thereof. These materials are commercially available from Aldrich Chemical Company (Milwaukee, Wis.) or Sigma Chemical Company (St. Louis, Mo.).

Another suitable skin care actives include hexylresorcinol, glycyrrhetinic acid, and tocopherol succinate.

Any other suitable optional component can also be included in the personal care composition of the present invention, such as those ingredients that are conventionally used in given product types. The Personal Care Product Council's *International Cosmetic Ingredient Dictionary and Handbook*, Thirteenth Edition, 2010, describes a wide variety of nonlimiting functional materials that can be added to the composition herein. Examples of these functional classes include, but are not limited to: abrasives, absorbents, fragrances, anti-acne agents, anti-caking agents, antifoaming agents, antimicrobial agents (e.g., iodopropyl butylcarbamate), antifungal agents, antioxidants, binders, buffering agents, bulking agents, chelating agents, colorants, cosmetic astringents, cosmetic biocides, denaturants, drug astringents, external analgesics, film formers, opacifying agents, pH adjusters, plant derivatives, plant extracts, plant tissue extracts, plant seed extracts, plant oils, botanicals, botanical extracts, preservatives, propellants, reducing agents, sebum control agents, sequestrants, skin bleaching agents, skin-conditioning agents (e.g. humectants and occlusive agents), and skin protectorants. Other suitable optional person care ingredients include materials listed in paragraphs 513-839 of U.S Patent Application No. 2010/0112100.

Methods of Using the Personal Care Compositions

The personal care compositions of the present invention are useful for improving or regulating a number of keratinous tissue conditions. As used in relation to methods of using the personal care compositions, "regulating" means maintaining skin appearance and/or feel of the keratinous tissue with little to no degradation in appearance and/or feel, and "improving" means affecting a positive change in keratinous tissue appearance and/or feel. The keratinous tissue appearance and/or feel benefit may be an acute or chronic benefit. In other embodiments, the personal care composition may result in a physiological change of the keratinous tissue.

Keratinous tissue conditions that may be regulated or improved include, but are not limited to thickening keratinous tissue (e.g., building the epidermis and/or dermis and/or subcutaneous layers of the skin and where applicable the keratinous layers of the nail and hair shaft), atrophy, softening and/or smoothing, itch, appearance of dark under-eye circles and/or puffy eyes, sallowness, sagging (e.g., glycation), tanning, desquamating, exfoliating, and/or increasing turnover in mammalian skin, pores size, oily/shiny appearance, hyperpigmentation such as post-inflammatory hyperpigmentation, spider vessels and/or red blotchiness on mammalian skin, fine lines and wrinkles, dryness (e.g., roughness, scaling, flaking), cellulite, and acne.

Other keratinous conditions that may be regulated or improved include signs of skin aging including, but not limited to, all outward visibly and tactilely perceptible manifestations, as well as any macro- or micro-effects, due to keratinous tissue aging. These signs may result from processes which include, but are not limited to, the development of textural discontinuities such as wrinkles and coarse deep wrinkles, fine lines, skin lines, crevices, bumps, large pores, unevenness or roughness; loss of skin elasticity; discoloration (including undereye circles); blotchiness; sallowness; hyperpigmented skin regions such as age spots and freckles; keratoses; abnormal differentiation; hyperkeratinization; elastosis; collagen breakdown, and other histological changes in the stratum corneum, dermis, epidermis, vascular system (e.g., telangiectasia or spider vessels), and underlying tissues (e.g., fat and/or muscle), especially those proximate to the skin.

The personal care compositions of the present invention are useful for improving or regulating insult-affected keratinous tissue. "Insult-affected keratinous tissue," means keratinous tissue which exhibits discomfort, irritation, an unpleasant or irregular appearance, and the like, for example after exposure to a physical and/or chemical irritant. Non-limiting examples of insult-affected keratinous tissue include burn (e.g., sunburns, windburn, chemical or thermal burns); rashes (e.g., diaper rash, shaving rash and allergen-induced rashes); discoloration (e.g., bleaching, staining, hyperpigmentation); nicks and cuts (e.g., shaving insults); and dry, chapped or rough skin (e.g., due to exposure to example wind, cold and/or low humidity). Non-limiting examples of insults include radiation, wind, low humidity, allergens, pollutants, chemical and natural irritants, bodily fluids, bodily waste, excessive moisture, bacteria, fungi, etc.

Method of Making the Personal Care Compositions

As presented above, the personal care composition may take a variety of forms. The following methods are exemplary and are not to be read as limiting. When the personal care composition is in the form of an oil dispersion or solution, the following method may be used. A sufficient amount of isosorbide diester is provided to solubilize the solid UV active. In a suitable vessel, the solid UV active is combined with the isosorbide diester. The combination may be mixed (e.g., magnetic stirrer with spin bar) and optionally heated to 70° C. Additional materials soluble and/or compatible may also be added. The composition is mixed until no solute is visible. Mixing or homogenization may be done by devices and techniques known in the art. Suitable methods and devices include mechanical techniques such as mixers or shaker plate, high pressure techniques such as sonolators or liquid whistles, and ultrasonic techniques such as sonicators. Typically mixing and the optional heating at 70° C. are performed for no more than 10 minutes. The composition may be transferred to an acceptable container. The composition may be cooled.

When the personal care composition is in the form of an emulsion, the oil phase may be prepared according to the method above. A separate vessel the aqueous phase is prepared by combining the aqueous carrier such as water and/or a water miscible solvent with any water soluble materials, if present. The combination may be mixed (e.g., magnetic stirrer with spin bar) and optionally heated to 70° C. Depending upon the particular emulsion form (O/W or W/O) an emulsifier may be added to the suitable phase. Typically, the emulsifier may be added to the continuous phase. Again, depending upon the desired emulsion form, the oil phase may be added to the aqueous phase or vice versa. The emulsion may be mixed (e.g., magnetic stirrer with spin bar) and optionally heated to 70° C. The composition is mixed until no solute is visible. Mixing or homogenization may be done by devices and techniques known in the art. Typically mixing and the optional heating at 70° C. are performed for no more than 10 minutes. The emulsion may be transferred to an acceptable container. The emulsion may be cooled.

Examples 1-3 are personal care compositions providing a UV protection benefit.

|  | Example 1 | Example 2 | Example 3 |
|---|---|---|---|
| Water Phase: | | | |
| Water | qs | qs | qs |
| Glycerin | 5.0 | 5.0 | 5.0 |
| Disodium EDTA | 0.1 | 0.1 | 0.1 |
| Methylparaben | 0.2 | 0.2 | 0.2 |
| Niacinamide | 4.0 | 4.0 | 4.0 |
| D-panthenol | 0.5 | 0.5 | 0.5 |
| Phenylbenzimidazole Sulfonic Acid | 1.0 | 1.0 | 1.0 |
| Pentylene Glycol | 1.0 | 1.0 | 1.0 |
| Benzyl alcohol | 0.25 | 0.25 | 0.25 |
| Triethanolamine | 0.64 | 0.64 | 0.64 |
| Oil Phase: | | | |
| Isopropyl Isostearate | 1.33 | 1.33 | 1.33 |
| Octisalate | 4.0 | 4.0 | 4.0 |
| Octocrylene | 1.0 | 1.0 | — |
| Avobenzone | 2.0 | 2.0 | — |
| Vitamin E Acetate | 0.1 | 0.1 | 0.1 |
| Ethylparaben | 0.2 | 0.2 | 0.2 |
| Propylparaben | 0.2 | 0.2 | 0.2 |
| Cetyl alcohol | 0.3 | 0.3 | 0.3 |
| Stearyl alcohol | 0.4 | 0.4 | 0.4 |
| Behenyl alcohol | 0.4 | 0.4 | 0.4 |
| Cetearyl Glucoside/Cetearyl Alcohol[1] | 0.3 | 0.3 | 0.3 |
| PEG-100 stearate | 0.3 | 0.3 | 0.3 |
| Tinosorb S[5] | — | 1 | 2 |
| Synovea DOI[6] | 4.0 | 5.0 | 6.0 |
| Thickener: | | | |
| Sepigel™ 305[2] | 2.25 | 2.25 | 2.25 |
| Additional Ingredients: | | | |
| Microthene FN510[3] | 1.0 | 1.0 | 1.0 |
| Polysorbate 20 | 0.5 | 0.5 | 0.5 |
| Dow Corning™ 1503[4] | 2.0 | 2.0 | 2.0 |
| Total: | 100% | 100% | 100% |

[1]Emulgade™ PL68/50 from Cognis™
[2]Polyacrylamide, C13-14 isoparaffin, and laureth-7 from Seppic™
[3]Polyethylene homopolymer spheres from Equistar™
[4]Dimethicone and dimethiconol from Dow Corning™
[5]Bis-Ethylhexyloxyphenol Methoxyphenyl Triazine from BASF™
[6]Dioctanoyl Isosorbide from Syntheon, Ltd., Boonton, NJ.

In a suitable vessel, the water phase ingredients are combined and heated to 75° C. In a separate suitable vessel, the oil phase ingredients are combined and heated to 75° C. Next the oil phase is added to the water phase and the resulting emulsion is milled (e.g., with a Tekmar T-25). The thickener is then added to the emulsion and the emulsion is cooled to 45° C. while stirring. At 45° C., the remaining additional ingredients are added. The product is then cooled with stirring to 30° C., milled again, and then poured into suitable containers.

TEST EXAMPLES

In the testing provided below, "soluble" (or "solubilize"), in relation to the solubility of a solid solute being tested, means that no visible crystals may be seen after a prescribed storage period at a storage condition. The storage period can vary. Suitable storage periods include about 24 hours, about 1 week, and about 30 days. Suitable storage conditions include ambient conditions or cold storage at 5° C. (approximately 1 atm). In certain embodiments, solubility may be determined after a 24 hour storage period at ambient conditions. In other embodiments, solubility may be determined after 20 days in cold storage. Other testing parameters may include storage for prolonged time periods (e.g., 30 day, 50 days, 60 days, 90 days) and at variable temperatures (e.g., 5° C., 50° C.).

Example 1

The solvency of an isosorbide diester within the scope of the present invention was tested against two conventional, industry standard solvents. The solvency of isosorbide dicaprylate, isopropyl lauroyl sarcosinate, and C12-15 alkyl benzoate was tested using butyl methoxydibenzoylmethane (i.e., avobenzone, commercially available as PARSOL® 1789 from DSM) as the solid UV active. Various ratios of the solute:solvent were prepared by mixing solvents and the solid sunscreen (solute) and heating to 70° C. Upon reaching 70° C., the examples may be mixed for about 10 minutes. The mixtures are placed in a covered vial and cooled to the storage temperature. Solubility was evaluated for samples stored 24 hours after mixing at room temperature. Solubility was also evaluated for samples stored for 7 day at 5° C. followed by equilibration to ambient conditions. Results are shown in Table 1. The data demonstrates that the solvency of the isosorbide diester is equivalent to the industry leading solvents.

TABLE 1

| | Solute:Solvent Ratio | | | | | |
|---|---|---|---|---|---|---|
| | 24 hour rest at Ambient Conditions | | | 30 day storage at 5° C. | | |
| | 1:2 | 1:3 | 1:4 | 1:2 | 1:3 | 1:4 |
| 1A. Isosorbide dicaprylate | X | S | S | NT | X | S |
| 1B. Isopropyl lauroyl sarcosinate* | S | S | S | X | S | S |
| 1C. C12-15 alkyl benzoate* | X | S | S | NT | X | S |

*Comparative Examples
S = soluble
X = crystals present
NT = Not Tested

Example 2

The solvency of an isosorbide diester within the scope of the present invention was tested against two conventional, industry standard solvents. The solvency of isosorbide dicaprylate, isopropyl lauroyl sarcosinate, and C12-15 alkyl benzoate was tested when using bis-ethylhexyloxyphenol methoxyphenyl triazine (i.e., bemotrizinol, commercially available as Tinosorb® S from BASF as the solid UV active. Various ratios of the solute:solvent were prepared by mixing solvents (e.g., magnetic stir plate with stir bar) and the solid sunscreen (solute) and heating to 70° C. Upon reaching 70° C., the examples may be mixed for about 10 minutes. The mixtures are placed in a covered vial and cooled to the storage temperature. Solubility was evaluated for samples stored 24 hours after mixing at room temperature. Solubility was also evaluated for samples stored for 7 day at 5° C. followed by equilibration to ambient conditions. Results are shown in Table 2. The data demonstrates that the solvency of the isosorbide diester is superior to the industry leading solvents.

TABLE 2

| | Solute:Solvent Ratio | | | | | | | |
|---|---|---|---|---|---|---|---|---|
| | 24 hour rest at Ambient Conditions | | | | 30 day storage at 5° C. | | | |
| | 1:3 | 1:4 | 1:6 | 1:8 | 1:3 | 14 | 1:6 | 1:8 |
| Isosorbide dicaprylate | S | S | S | S | S | S | S | S |
| Isopropyl lauroyl sarcosinate* | NT | S | S | S | NT | X | S | S |
| C12-15 alkyl benzoate* | NT | S | S | S | NT | X | S | S |

*Comparative Examples
S = soluble
X = crystals present
NT = Not Tested

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal care composition comprising:
   a. an isosorbide diester solvent having the formula:

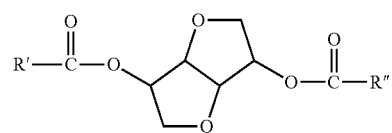

wherein R' and R" are independently selected from a straight or branched $C_{1-30}$ chain, which may be saturated or unsaturated;
   b. a solid UV active soluble in the isosorbide diester solvent, wherein the isosorbide diester solvent is present in an amount sufficient to solublize the solid UV active and the amount of isosorbide diester solvent is at least 2 parts, by weight, isosorbide diester solvent to every 1 part, by weight, solid UV active; and
   c. a dermatologically acceptable carrier.

2. The personal care composition of claim 1 wherein R' and R" are the same.

3. The personal care composition of claim 1 wherein R' and R" are a saturated straight or branched C7 chain.

4. The personal care composition of claim 3 wherein R' and R" are a saturated straight C7 chain.

5. The personal care composition of claim 1 comprising from about 0.1% to about 10% of the solid UV active.

6. The personal care composition of claim 1 wherein the solid UV active is selected from 4-tert-butyl-4'-methoxy dibenzoylmethane, bis-ethylhexyloxyphenol methoxyphenyl triazine, 2,4,6-trianilino-(p-carbo-2'-ethylhexyl-1'-oxy)-1,3,5-triazine, diethylhexyl butamido triazone, diethylamino hydroxybenzoyl hexyl benzoate, benzophenone-3,4-methylbenzylidene camphor, ethylhexyl bis-isopentylbenzoxazolylphenyl melamine and combinations thereof.

7. The personal care composition of claim 1 wherein the solid UV active is 4-tert-butyl-4'-methoxy dibenzoylmethane, bis-ethylhexyloxyphenol methoxyphenyl triazine, and combinations thereof.

8. The personal care composition of claim 1 comprising at least 5 parts, by weight, isosorbide diester solvent to every 1 part, by weight, solid UV active.

9. The personal care composition of claim 1 comprising at least 10 parts, by weight, isosorbide diester solvent to every 1 part, by weight, solid UV active.

10. The personal care composition of claim 1 further comprising a photostabilizer.

11. The personal care composition of claim 10 wherein the photostabilizer is selected from a group consisting of methoxycrylene, diethylhexyl 2,6-naphthalate, diethylhexyl syringylidenemalonate, and combinations thereof.

12. The personal care composition of claim 11 comprising at least 1 part, by weight, photostabilizer to every 1 part, by weight, UV active.

13. The personal care composition of claim 1 further comprising an additional UV active.

14. The personal care composition of claim 13 wherein the additional UV active is selected from a dibenzoylmethane compound other than 4-tert-butyl-4'-methoxy dibenzoylmethane; 2-ethylhexyl-p-methoxycinnamate; octyldimethyl-p-aminobenzoic acid; 2-ethylhexyl-2-cyano-3,3-diphenylacrylate; 2-ethylhexyl salicylate; homomenthyl salicylate; 2-phenylbenzimidazole-5-sulfonic acid; 2-(p-dimethylaminophenyl)-5-sulfonicbenzoxazoic acid; disodium phenyl dibenzimidazole tetrasulfonate; sodium dihydroxy dimethoxy disulfobenzophenone; polysilicone-15; isoamyl p-methoxycinnamate; titanium dioxide, zinc oxide; methylene bis-benzotriazolyl tetramethylbutylphenol; and combinations thereof.

15. The personal care composition of claim 13 wherein the additional UV active is 2-ethylhexyl-2-cyano-3,3-diphenylacrylate.

16. The personal care composition of claim 1 in the form of an emulsion comprising:
    a. an aqueous phase comprising water; and
    b. an oil phase comprising the isosorbide diester solvent and the solid UV active soluble in the isosorbide diester solvent.

17. A personal care composition in the form of an emulsion comprising:
    a. an aqueous phase comprising water; and
    b. an oil phase comprising:
        i. from about 0.1% to about 10% of a UV active selected from 4-tert-butyl-4'-methoxy dibenzoylmethane, bis-ethylhexyloxyphenol methoxyphenyl triazine, and combinations thereof,
        ii. a sufficient amount of an isosorbide diester solvent to solublize the UV active, wherein the isosorbide diester solvent is present in amount of at least 2 parts, by weight, isosorbide diester solvent to every 1 part, by weight, solid UV active and the isosorbide diester has the formula:

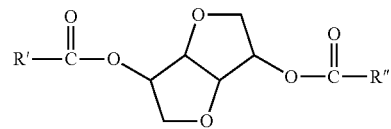

wherein R' and R" are a saturated straight or branched $C_7$ chain.

18. A method of making a personal care composition comprising the steps of:
    a. providing a solid UV active;
    b. combining a sufficient amount of an isosorbide diester solvent to solublize the solid UV active to form an oil phase, wherein the isosorbide diester is present in an amount of at least 2 parts, by weight, isosorbide diester solvent to every 1 part, by weight, solid UV active and has the formula:

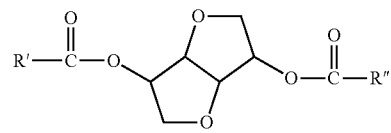

wherein R' and R" are independently selected from a straight or branched $C_{1-30}$ chain, which may be saturated or unsaturated; and
    c. homogenizing the oil phase until the solid UV active is dissolved.

19. The method of claim 18 further comprising the step of combining the oil phase with an aqueous phase comprising at least 1% water, by weight of the personal care composition.

20. The method of claim 18 wherein the solid UV active is selected from 4-tert-butyl-4'-methoxy dibenzoylmethane, bis-ethylhexyloxyphenol methoxyphenyl triazine, 2,4,6-trianilino-(p-carbo-2'-ethylhexyl-1'-oxy)-1,3,5-triazine, diethylhexyl butamido triazone, diethylamino hydroxybenzoyl hexyl benzoate, benzophenone-3,4-methylbenzylidene camphor, ethylhexyl bis-isopentylbenzoxazolylphenyl melamine and combinations thereof.

21. The method of claim 18 wherein the solid UV active is selected from 4-tert-butyl-4'-methoxy dibenzoylmethane, bis-ethylhexyloxyphenol methoxyphenyl triazine, and combinations thereof.

22. The method of claim 18 wherein R' and R" are the same.

23. The method of claim 18 wherein R' and R" are a saturated straight or branched C7 chain.

24. The method of claim 18 wherein R' and R" are a saturated straight C7 chain.

25. A personal care composition comprising:
    a. an isosorbide diester solvent having the formula:

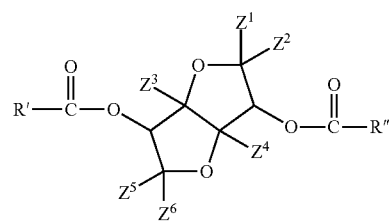

wherein R' and R" are independently selected from a straight or branched $C_{1-30}$ chain which may be saturated or unsaturated and $Z^1$—$Z^6$ are independently selected from hydrogen, hydroxyl, amino, amido, R', or R";
b. a solid UV active soluble in the isosorbide diester solvent, wherein the amount of isosorbide diester solvent is least 2 parts, by weight, isosorbide diester solvent to every 1 part, by weight, solid cosmetic active; and
c. a dermatologically acceptable carrier.

26. The composition of claim 2 wherein R' and R" each is a saturated straight C7 chain.

27. The composition of claim 1 wherein the isosorbide diester is isosorbide dicaprylate.

* * * * *